US009155779B2

(12) United States Patent
Rueter et al.

(10) Patent No.: US 9,155,779 B2
(45) Date of Patent: Oct. 13, 2015

(54) YERSINIA OUTER PROTEIN M (YOPM) IN THE TREATMENT OF PSORIASIS

(56) References Cited

U.S. PATENT DOCUMENTS

| | | | | |
|---|---|---|---|---|
| 2007/0122881 A1* | 5/2007 | Surber | ............................ | 435/69.1 |
| 2010/0112002 A1* | 5/2010 | Lien et al. | ................... | 424/234.1 |
| 2011/0020273 A1* | 1/2011 | Chang et al. | .................. | 424/85.2 |

OTHER PUBLICATIONS

Cromme, C., et al., (2011) Anti-Inflammatory Effects of YopM in Rheumatoid Arthritis Fibroblast-Like Synoviocytes, Ann Rheum Dis 70 (Suppl. 2): A1-A94.

Kerschen, E.J., et al., (2004) *The plague virulence protein, YopM, targets innate immunity by suppressing proinflammatory cytokine and IL-15 production and depleting NK cells*, FASEB Journal (Experimental Biology 2004: Meeting Abstract #773.8) 18: A1141.

Poceva, M., et al., (2011) *YopM as a bacteria-derived anti-inflammatory cell-penetrating peptide (CPP) in a murine Psoriasis model*, IJMM International Journal of Medical Microbiology (Meeting Abstract #FTP07) 301 (Suppl. 47): 26.

Rueter, C., et al., (2010) *A newly identified bacterial cell-penetrating peptide that reduces the transcription of pro-inflammatory cytokines*, Journal of Cell Science 123: 2190-2198.

Schamert, J., et al., (2009) *YopM from Yersinia enterocolitica penetrates host cell membranes and down-regulates transcription of pro-inflammatory cytokines*, IJMM International Journal of Medical Microbiology (Meeting Abstract #IIP12) 299 (Suppl. 46): 33.

Schmidt, M.A., (2012) *Sekretionsmechanismen Gram-negativer Pathogene*, (from: campus.uni-muenster.de/uploads/media/09012012_Netzfolien.pdf).

\* cited by examiner

Fig. 1

Figure 1: Domain organization and functional regions of YopM

Type-III secretion (S) and translocation (T) signal required by the T3SS [N-terminal residues aa 34-40 (S) & aa 40-100 (T), (Ghosh 2004)]. NLS, nuclear localisation signal. NLS-I: three N-terminal LRRs and NLS-II: 32 C-terminal residues of YopM. Interaction with serum proteins α-thrombin and α1-antitrypsin seems to depend on conserved residues in LRR domains and not on specific domains of the LRR-containing region of the protein. The figure describes information gained from analyses of YopM from all three pathogenic *Yersinia* species and summarizes work cited in the introduction.

Fig.2

Figure 2. Purification of recombinant YopM. a) SDS-PAGE analysis following isolation and purification of YopM. Proteins were separated on a 12.5% SDS polyacrylamide gel and subsequently silver stained. lane M: "See Blue Plus2" protein ladder, RE: crude extract, W: wash I , lanes E2-5: elution fractions 2-5. b) Determination of LPS content in YopM elution fractions by Limulus amebocyte lysate Toxin sensor assay.

Fig.3

Figure 3: Effect of YopM on an imiquimod (IMQ)- induced psoriasis mouse model. Daily topical application of imiquimod (5% Aldara Creme Sachets b-f), a TLR7/8 ligand and potent immune activator, on mouse back skin (Balb/c) induces and exacerbates psoriasis (b). After induction of psoriatic skin, YopM was applied to different groups of mice either by intra-peritoneal injection (c; i.p. 100 µg in PBS every 48 h), as a YopM-containing cream (e; mice were balmed with 200 mg cream containing approx. 30 µg of YopM), or by subcutaneous injection (f; s.c. 25 µg in PBS every 48 h). (a) negative control (untreated mice). (d) placebo control (200 mg cream without YopM).

Fig.4

Figure 4: Histological analyses of psoriatic skin tissues. In order to determine the beneficial effects of YopM on epidermal proliferation, and abnormal differentiation, the epidermis of back-skin tissue sections (5μm) was stained using a PAN Cytokeratin Antibody (green). The nuclei were stained with Draq5 (blue). (a) negative control; (b) IMQ-positive control; (C) YopM intraperitoneally injected; (d) placebo, (e) YopM balmed, and (f) YopM subcutaneously injected. Pictures were taken with confocal laser scanning microscope. Magnification 40X.

Fig.5

Figure 5: Histological analyses of psoriatic skin tissues. In order to determine the amount of epidermal infiltrates consisting of CD4+ T cells induced by IMQ, the epidermis of back-skin tissue sections (5μm) was stained using CD4+ (green) and IL17 (red) antibodies. The nuclei were stained with Draq5 (blue). (a) negative control; (b) IMQ-positive control; (C) YopM intraperitoneally injected; (d) YopM balmed. Pictures were taken with confocal laser scanning microscope. Magnification 40X.

Fig.6

Figure 6: Distribution of YopM in the Epidermis and Dermis after 48 h of application. YopM specific immunostaining (green) of skin tissue samples. YopM balmed: Epidermis (a), Dermis (b); YopM i.p. injected: Epidermis (c), Dermis (d); YopM s.c. injected: Epidermis (e), Dermis (f); negative control: Epidermis (g), Dermis (h). Actin was stained with Texas Red Phalloidin (red). DNA was stained with Draq5 (blue). Pictures were taken with confocal laser scanning microscope. Magnification 40X.

Figure 7: Distribution of YopM in the epidermis and dermis after 48 h of application. YopM specific immunostaining (green) of skin tissue samples. untreated IMQ-skin: epidermis (a), dermis (d), subcutis (g), and local lymph nodes (j). YopM applied epicutaneously: epidermis (b), dermis (e), subcutis (h), and local lymph nodes (k).YopM subcutaneously injected: epidermis (c), dermis (f), subcutis (i), and local lymph nodes (l).Actin was stained withTexas Red Phalloidin (red). DNA was stained with Draq5 (blue). Pictures were taken with a confocal laser scanning microscope. Magnification 40X.

Figure 8: Effect of YopM on papillomatosis. IMQ treatment induces regular and symmetrical extensions of rete ridges, separated by elongated dermal papillae (papillomatosis). H&E staining of the back skin of mice after different treatment regimes. A line indicates regular and symmetrical extensions of rete ridges and the elongated dermal papillae. (a) healthy skin; (b) untreated IMQ-skin; (c) placebo control; (d) YopM applied epicutaneously; (e) 12.5 ƒŶg YopM subcutaneously injected; (f) (e) 100 µg YopM subcutaneously injected. Pictures were taken with a light microscope. Magnification 40X.

YERSINIA OUTER PROTEIN M (YOPM) IN THE TREATMENT OF PSORIASIS

This application claims benefit from International Application No. PCT/EP2012/053209, which was filed on Feb. 24, 2012, which in turn claims priority to U.S. Provisional Patent Application No. 61/539,693, filed on Sep. 27, 2011; and European Patent Application 11007785.6 filed on Sep. 23, 2011; wherein the entireties of said patent applications are incorporated herein by reference.

1. FIELD OF THE INVENTION

The present invention relates to the use of *Yersinia* outer protein M (YopM) in the prevention and/or treatment of psoriasis by cutaneous, intradermal or subcutaneous administration.

2. BACKGROUND ART

The YopM protein consists of two amino terminal helices followed by variable numbers of an approximately 20 amino acid leucine-rich repeat (LRR) motif (12-20 LRR among different *Yersinia* strains), forming a horseshoe-shaped protein. The LRR, which have been implicated in protein-protein interactions, make up most of YopM (FIG. 1).

Besides protein-protein interactions with serum proteins such as α-thrombin and α1-antitrypsin (Hines et al., 2000; Heusipp et al., 2006) and a scaffolding function of YopM with two cytoplasmic kinases, RSK1 and PRK2 (McDonald et al., 2003) the molecular function of YopM during infection is only poorly understood.

The fact that yopM mutants of *Y. enterocolitica* and *Y. pestis* cannot establish a systemic infection in infected mice (Trulzsch et al., 2004; Kerschen et al., 2004) indicates that YopM is important for full virulence and resistance to innate immunity during infection (Leung et al., 1990). Interestingly, Kerschen et al. showed that YopM of Y. pestis caused a global depletion of natural killer (NK) cells (Kerschen et al., 2004). In association with this NK cell depletion, the spleen/liver tissues of infected mice and in the same manner the macrophages/NK cells isolated from those tissues showed a decreased expression of several proinflammatory cytokines including TNF-α, IFN-γ, IL-1β, IL-12, IL-15, IL-15Rα and IL-18.

How YopM interferes with the signalling pathways of the proinflammatory cytokines is just speculative and has not been investigated. Specifically, it remains elusive how YopM as a locally delivered, bacterial host-cell-contact dependently translocated protein can have a global effect on the host response (Kerschen et al., 2004).

According to a model of *Y. enterocolitica* infection, YopM is translocated through the T3SS into the host cell cytoplasm. However, other studies also suggest an additional extracellular role of YopM, like binding to the acute-phase protein α1-antitrypsin, and binding of YopM to serum protein α-thrombin which ist supported by a humoral immune response to YopM after infection of mice (Benner et al., 1999, Heusipp et al., 2006; Huck et al. 1998). Furthermore, an apolar secretion (7%) of YopM during in vitro infection has been described by Cheng and Schneewind (Cheng & Schneewind, 2000).

Patent Application having publication number WO2009/115531 reports an additional delivery function of YopM which is independent from the direct delivery of the effector protein by T3SS into the cytoplasm of host cells. In particular, WO2009/115531 discloses *Yersinia* outer protein M (YopM), a YopM fragment or a YopM variant which are capable of auto penetrating the cell membrane and integrating into the cell cytosol without the requirement of additional factors. The use of this function for delivering a cargo molecule across the membrane to the cytosol of a cell is described therein. WO2009/115531 further discloses that once YopM is integrated into the cell cytosol, YopM is capable of effectively downregulating cytokines, in particularly pro-inflammatory cytokines.

Psoriasis is one of the most common immune-mediated chronic inflammatory skin disorders affecting approximately 2-3% of the population. It is considered as an incurable, life-long skin condition that affects all races, age groups and both sexes. The pathogenesis of psoriasis is complex and not clearly understood. Ongoing research indicates that immune T-cells appear to play a dominant role for the development of this disease. These cells release TNF-α, IFN-α and other pro-inflammatory cytokines that lead to vasodilation, leukocyte migration, and activation of keratinocytes. This further activates dendritic cells which in turn leads to inflammation.

Psoriasis appears in a variety of forms with distinct characteristics. Typically, an individual has only one type of psoriasis at a time.

Plaque psoriasis (psoriasis vulgaris) is the most prevalent form of the disease. About 80 percent of those who have psoriasis have this type. It is characterized by raised, inflamed, red lesions covered by a silvery white scale. It is typically found on the elbows, knees, scalp and lower back.

Guttate psoriasis is a form of psoriasis that often starts in childhood or young adulthood. This form of psoriasis appears as small, red, individual spots on the skin. Guttate lesions usually appear on the trunk and limbs. These spots are not usually as thick as plaque lesions.

Guttate psoriasis often comes on quite suddenly. A variety of conditions can bring on an attack of guttate psoriasis, including upper respiratory infections, *streptococcal* throat infections (strep throat), tonsillitis, stress and injury to the skin.

Inverse psoriasis is found in the armpits, groin, under the breasts, and in other skin folds around the genitals and the buttocks. This type of psoriasis appears as bright-red lesions that are smooth and shiny. Inverse psoriasis is subject to irritation from rubbing and sweating because of its location in skin folds and tender areas. It can be more troublesome in overweight people and those with deep skin folds.

Primarily seen in adults, pustular psoriasis is characterized by white blisters of noninfectious pus (consisting of white blood cells) surrounded by red skin. It may be localized to certain areas of the body, such as the hands and feet, or covering most of the body. It begins with the reddening of the skin followed by formation of pustules and scaling.

Erythrodermic psoriasis is a particularly inflammatory form of psoriasis that affects most of the body surface. The reddening and shedding of the skin are often accompanied by severe itching and pain, heart rate increase, and fluctuating body temperature.

Erythrodermic psoriasis causes protein and fluid loss that can lead to severe illness. The condition may also bring on infection, pneumonia and congestive heart failure.

Several drugs have been used in the treatment of psoriasis. The four most commonly prescribed systemic medications to treat psoriasis are Methotrexate, Ciclosporin, Acitretin and Hydroxycarbamide. Methotrexate, Ciclosporin and Hydroxycarbamide all work by suppressing the immune system, whereas Acitretin is a Vitamin A derived treatment.

A common disadvantage (besides their side effects) of all drugs currently available for treating this primarily cutaneous disease is that they are only effective when given systemically but are largely ineffective when applied topically because of poor absorption.

Systemic medications are prescription medications that affect the entire body. The systemic treatments that are available to treat psoriasis and psoriatic arthritis are associated with significant short- and long-term side effects. The benefits of psoriasis clearance or improvement must be balanced against the risk of these side effects.

There is therefore the need of an effective therapeutic agent useful in the prevention and/or treatment of psoriasis having a good patient compliance and reduced side effects.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein. Unless otherwise indicated, the term "at least" preceding a series of elements is to be understood to refer to every element in the series. At least one includes for example, one, two, three, four, or five or even more. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

3. DESCRIPTION OF THE INVENTION

The present inventors have surprisingly found that *Yersinia* outer protein M (YopM) when administered via cutaneous, intradermal or subcutaneous route prevents and/or treats psoriasis. Even more surprisingly, it has been found by the present inventors that the cutaneous, intradermal, or subcutaneous routes of administration provide an improved method of prevention and/or treatment of psoriasis when compared to the intra-peritoneal route. Interestingly, in contrast to sub-cutaneous treatment, epicutaneously applied YopM did not enter systemic distribution, mainly remained in the epidermis, dermis, and subcutis, and couldn't be found in local lymph nodes. As sub-cutaneous injected YopM was also found in local lymph nodes, an epicutaneous treatment with YopM is clearly advantageous and favoured to avoid unwanted side effects. The cutaneous administration route is therefore the preferred administration route of the present invention.

It has been found that *Yersinia* outer protein M (YopM) when administered via cutaneous, intradermal or subcutaneous route is able to treat psoriasis in a patient affected by this disease. A "patient" thereby includes mammals like for example mouse, rat, cat, dog, apes and humans, humans being preferred.

In particular, the *Yersinia* outer protein M (YopM) is able to treat plaque psoriasis, guttate psoriasis, inverse psoriasis, pustular psoriasis, erythrodermic psoriasis, arthritis psoriasis.

In one aspect of the invention, *Yersinia* outer protein M (YopM) is selected from YopM of the species *Yersinia enterocolitica, Yersinia pseudotuberculosis* or *Yersinia pestis*.

YopM is administered in a dose effective to prevent and/or treat psoriasis. The dose for cutaneous administration ranges from 1 µg/cm$^2$ to 20 mg/cm$^2$, preferably 1 µg/cm$^2$ to 20 µg/cm$^2$, more preferably about 2 µg/cm$^2$.

The term "*Yersinia* outer protein M (YopM)" according to the invention relates to a *Yersinia* outer protein M. The term includes the *Yersinia* outer protein M full-length amino acid sequence, YopM fragments and YopM variants thereof. The term includes a *Yersinia* outer protein M as described in Boland A, et al. EMBO J. 1996 Oct. 1; 15(19):5191-201; Cornelis GR. J. Bacteriol. 1998 November; 180(21):5495-504; Skrzypek, E., Cowan, C. and Straley, S. C. (1998) Mol. Microbiol. 30: 1051-1065; McDonald, C, Vacratis, P. O., Bliska, J. B. and Dixon, J. E. (2003) J. Biol. Chem 278: 18514-18523; Skrzypek E, Myers-Morales T, Whiteheart S W, Straley S C. Infect. Immun. 2003 February; 71(2):937-47; Kerschen, E. J., Cohen, D. A., Kaplan, A. M. and Stranley, S. C. (2004) Infect. Immun. 72: 4589-4602; Heusipp, G., Spekker, K., Brast, S., Falker, S. and Schmidt, M. A. (2006) Microbiol. 152: 1327-1335; Kloss E, Barrick D. Protein Sci. 2009 September; 18(9):1948-60; McCoy et al. Infect Immun. 2010 June; 78(6):2584-98; McPhee J B et al. Infect Immun. 2010 August; 78(8):3529-39; Ruter C et al. J Cell Sci. 2010 Jul. 1; 123(Pt 13):2190-8; Hentschke M et al. PLoS One. 2010 Oct. 5; 5(10). pii: e13165 and Vieux E F et al. Biophys Chem. 2011 November; 159(1):152-61; or derivable from any biological database known to the person skilled in the art, e.g. from the Genbank database.

In a preferred embodiment, *Yersinia* outer protein M (YopM) is a *Yersinia* outer protein M of a *Yersinia* strain naturally comprising a YopM encoding virulence plasmid. The term "YopM encoding virulence plasmid" relates to plasmid pYV or pCD1 as described to be present, for instance, in *Yersinia enterocolitica, Yersinia pseudotuberculosis* and *Yersinia pestis* (Cornelis et al., Microbiol. Mol. Biol. Rev. 62:1315-1352 (1998)).

In a further preferred embodiment, the *Yersinia* outer protein M (YopM) is a *Yersinia* outer protein M selected from the species *Yersinia enterolitica, Yersinia pseudotuberculosis* and *Yersinia pestis*. More preferably, *Yersinia* outer protein M (YopM) is a *Yersinia* outer protein M selected from *Yersinia enterolitica* 8081 v, serotype O:8.

In a further embodiment of the invention, a YopM fragment is used in the prevention and treatment of psoriasis. In the context of the present invention, the term "YopM fragment" means that the fragment is a therapeutically active fragment of the YopM full length protein.

The term "therapeutically active" means that the fragment has the above mentioned therapeutically activities of YopM full length amino acid sequence protein, i.e. a fragment of the invention has the capability of preventing and/or treating psoriasis. Hence a "YopM fragment" according to the present invention is a YopM fragment that retains the property of the full length YopM protein to preventing and/or treating psoriasis. In particular, a YopM fragment of the invention is able to treating psoriasis in the mouse model used in Example paragraph 5.2 below. In a particular embodiment, the fragment retains or comprises or consists of the "immunomodulatory domain" of the YopM full length protein or the fragment retains or comprises or consists of a part of the "immunomodulatory domain" of the YopM full length protein. An "immunomodulatory domain of YopM" comprises at least one leucine-rich repeat (LRR) of YopM, i.e. one, two, three, four, five, six, seven or eight LRRs up to 20 LRRs. In an embodiment, the YopM fragment may also retain the property of YopM full length protein to allow translocation into the cytosol and/or to and/or into the nucleus of a target cell. Translocation of a YopM fragment into the cytosol and/or nucleus of the target cell can be permitted if the fragment of YopM retains the domain or part of the domain of the YopM full length protein which permits translocation. Alternatively, the translocation function can be performed by a "cell penetrating peptide" (CCP) which is heterologous to Yersinia. Preferably, the YopM fragment of the invention is able to distribute in the cells of the epidermis and/or dermis and/or hypodermis, and/or is able to distribute in the cells present in the epidermis and/or dermis and/or hypodermis. In particular, the YopM fragment of the invention is able to distribute in at least one kind amongst the cells of the epidermis and/or dermis and/or hypodermis, and/or is able to distribute in at least one kind amongst the cells present in the epidermis and/or dermis and/or hypodermis, wherein the term "distribute" means that the YopM fragment of the invention is able to enter in the cytosol of a cell and optionally to reach and/or optionally to enter the nucleus of said cell. The cells of the epidermis, dermis and/or hypodermis and/or the target cells for the prevention and/or treatment of psoriasis are for examples melanocytes, Langerhans' cells, Merkel's cells, keratinocytes, T helper cells, T suppressor cells, T killer cells, T memory cells, B cells, macrophages, mast cells or any other cells of the local immune system. Hence, preferably the YopM fragment of the invention is able to distribute in at least one of the target cells of the epidermis and/or dermis and/or hypodermis, and/or is able to distribute in at least one of the target cells present in the epidermis and/or dermis and/or hypodermis to prevent and/or treat psoriasis. In addition, the YopM fragment of the invention is able to down-regulate at least one cytokine. A list of cytokines is disclosed below. In particular, the fragment of the invention is able to down-regulating TNFα. The "YopM fragment" according to the invention is a fragment of the corresponding YopM full length protein of at least 100 aminoacids, more preferably is of at least 150 aminoacids, more preferable is of at least 150-300 aminoacids.

In a further embodiment of the invention, a YopM variant is used in the prevention and/or treatment of psoriasis. In the context of the present invention the term "YopM variant" includes that the variant is a therapeutically active full length YopM protein variant or a fragment thereof, preferably the term means that the variant has the therapeutic activities of full length YopM protein or fragment thereof. It is envisaged that a variant of the invention has the capability of preventing and/or treating psoriasis. Hence a "YopM variant" according to the present invention is a YopM variant that retains the property of the full length YopM protein of preventing and/or treating psoriasis. In a particular embodiment, this variant retains or comprises or consists of the "immunomodulatory domain" of YopM full length protein or the variant retains or comprises or consists of part of the "immune-modulatory domain" of the YopM full length protein. An "immunomodulatory domain of YopM" comprises at least one leucine-rich repeat (LRR) of YopM, i.e. one, two, three, four, five, six, seven or eight LRRs up to 20 LRRs. The addition of further LRRs is also envisaged. Variants and fragments of said immunomodulatory domain are likewise envisaged. In a particular embodiment, the YopM variant may also retain the property of full length YopM protein to allow translocation into the cytosol and/or nucleus of a target cell. Translocation of a YopM variant into the cytosol of the target cell can be permitted if the variant of YopM retains the property of the protein which permits translocation. Alternatively, the translocation function can be performed by a "cell penetrating peptide" (CCP) which is heterologous to Yersinia. Such variants may include deletions, insertions, inversions, repeats, and substitutions selected according to general rules known in the art so as to have little effect on activity. For example, guidance concerning how to make phenotypically silent amino acid substitutions is provided in Bowie et al., (Science 247: 1306-1310 (1990)), wherein the authors indicate that there are two main strategies for studying the tolerance of an amino acid sequence to change. Preferably, the YopM variant of the invention is able to distribute in the cells of the epidermis and/or dermis and/or hypodermis, and/or is able to distribute in the cell present in the epidermis and/or dermis and/or hypodermis. In particular, the YopM variant of the invention is able to distribute in at least one kind amongst the cells of the epidermis and/or dermis and/or hypodermis, and/or is able to distribute in the cells present in the epidermis and/or dermis and or hypodermis, wherein the term "distribute" means that the YopM variant of the invention is able to enter in the cytosol of a cell and optionally to reach and/or optionally to enter the nucleus of said cell. The cells of the epidermis, dermis and/or hypodermis are for examples melanocyte, Langerhans' cell, Merkel's cell, keratinocytes, T helper cells, T suppressor cells, T killer cells, T memory cells, B cells, macrophages, mast cells or any other cells of the local immune system. Hence, the YopM variant of the invention is able to distribute in at least one of the target cells of the epidermis and/or dermis and/or hypodermis, and/or is able to distribute in at least one of the target cell present in the epidermis and/or dermis and/or hypodermis to prevent and/or treat psoriasis. In addition, the YopM variant of the invention is able to down-regulate at least one cytokine. A list of cytokines is disclosed below. In particular, the variant of the invention is able to down-regulate TNFa. The term "YopM variant" includes the "YopM variant" as defined in patent application WO2009/115531 which is incorporated herein by reference.

The invention also encompasses YopM polypeptides having a lower degree of identity but having sufficient similarity so as to perform one or more of the same functions performed by the YopM protein, fragment and variant as described herein above.

Thus, in a further embodiment the full length YopM, YopM fragment, or YopM variant as described herein, is capable of autopenetrating the cell membrane and of integrating into the cell cytosol without the requirement of additional factors and is capable of downregulating cytokines i.e. the compounds of the invention comprise in this embodiment the immunomodulatory domain(s) of YopM, particularly at least one leucine-rich repeat (LRR), i.e. one, two, three, four, five, six, seven or eight LRRs up to 20 LRRs. The addition of further LRRs is also envisaged.

The term "cytokines" relates to soluble proteins and peptides that act as humoral regulators, which, either under normal or pathological conditions, modulate the functional activities of individual cells and tissues and also mediate interactions between cells directly and regulate processes taking place in the extracellular environment. The term encompasses type 1 cytokines produced by Th1 T-helper cells, type 2 cytokines produced by Th2 T-helper cells, interleukins, chemokines or interferons, e.g. IL-1 ra (antagonist), CNTF, LIF, OSM, Epo, G-CSF, GH, PRL, IP10, 1309, IFN-alpha, IFN-beta, IFN-gamma, IL2, IL3, IL4, IL5, IL6, IL7, IL8, IL9, IL10, IL11, IL 12 (p35 +p40), IL13, IL14, IL15, IL16, IL17 A-F, IL18, IL19, IL20, IL21 , IL22, IL23 (p19 +p40), IL24, IL25, IL26, IL27 (p28 - EBI3), IL28A, IL28B, IL29, IL30, IL31, IL32, IL33, IL35 (p35 - EBI3), LT-alpha, LT-beta, LIGHT, TWEAK, APRIL, BAFF, TL1A, GITRL, OX40L, CD40L, FASL, CD27L, CD30L, 4-1 BBL, TRAIL, RANK, GM- CSF, M-CSF, SCF, IL1-alpha, IL1-beta, aFGF, bFGF, int-2, KGF, EGF, TGF-alpha, TGF-beta, TNF-alpha, TNF-beta, betacellulin, SCDGF, amphiregulin or HB-EGF, as is known to the person skilled in the art and can be derived, for example, from Tato, CM. & Cua, D.J. (Cell 132: 900; Cell 132: 500, Cell 132: 324, (2008)) or from Cytokines & Cells Online Pathfinder Encyclopaedia. "Pro-inflammatory cytokines" are also contemplated. The term "proinflammatory cytokine" means an immunoregulatory cytokines that favours inflammation. Typically, pro-inflammatory cytokines comprise IL- 1-alpha, IL-1-beta, IL-6, and TNF-alpha. These pro-inflammatory cytokines are largely responsible for early responses. Other pro-inflammatory mediators include LIF, IFN- gamma, IFN-alpha, OSM, CNTF, TGF-beta, GM-CSF, TWEAK, IL-11, IL-12, IL-15, IL-17, IL-18, IL-19, IL-20, IL-8, IL-16, IL-22, IL-23, IL-31, and IL-32 (Tato, CM. & Cua, DJ. Cell 132:900; Cell 132:500, Cell 132, 324 (2008)). These pro-inflammatory cytokines may act as endogenous pyrogens (IL-1 , IL-6, TNF-alpha), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. Preferably, the term "pro-inflammatory cytokine" relates to TNF-alpha, IL-15, IFN-gamma, IFN-alpha, IL-1-beta, IL-8, IL-16 and IL-22.

The term "downregulates" or "downregulating" means that the mRNA levels of an expressed gene, e.g. of a cytokine gene, and/or the protein levels expressed by such mRNAs is reduced in the presence of YopM as described herein. The downregulation of mRNA and/or protein expressed by that mRNA in the context of the YopM of the invention can be tested and determined by methods known to a person skilled in the art.

In the context of the invention the term "cutaneous administration" sometimes also referred to as "epicutaneous administration" (e.c.) means the application of suitable drug dosage forms directly onto the skin for either local (topical) or systemic effects. According to the present invention, cutaneous administration is preferred. Cutaneous topical administration is likewise preferred. The cutaneous administration is preferably repeated in constant intervals such as for example every 12 hours, i.e. after 12 hours, 24 hours, 36 hours, 48 hours, 60 hours etc. In a preferred embodiment the cutaneous administration is repeated every 24 hours (i.e. daily administration).

Any pharmaceutical composition suitable for cutaneous administration is encompassed by the present invention. Suitable pharmaceutical compositions are e.g., cream, lotion, gel, paste, ointment, patch, spray, solution. Creams are semi-solid emulsions, that is mixtures of oil and water. They are divided into two types: oil-in-water (O/W) creams which are composed of small droplets of oil dispersed in a continuous phase, and water-in-oil (W/O) creams which are composed of small droplets of water dispersed in a continuous oily phase—both types are specifically included into the scope of the present invention. Creams, lotions, gels and ointments are preferred. The aforementioned pharmaceutical compositions comprise in a preferred embodiment cetearyl alcohol, paraffinum liquidum, glycerol, dimethicone, sodium cetearyl sulfate, phenoxyethanol, methylparaben, ethylparaben, propylparaben, and sodium hydroxide.

Any pharmaceutical composition suitable for sub-cutaneous administration is encompassed by the present invention. Suitable pharmaceutical compositions are e.g. solutions for subcutaneous injection. The solution may be administered for example in a pre-filled, multi-dose pen that delivers the effective dose of the YopM of the invention.

Any pharmaceutical composition suitable for intradermal administration is encompassed by the present invention. Pharmaceutical compositions suitable for intradermal administration are known in the art.

Further non-limiting examples of dosage forms include dispersions, liquid dosage forms suitable for cutaneous or intradermal or subcutaneous administration such as suspensions (e.g. aqueous or non-aqueous liquid suspensions, oil-in-water emulsions or a water-in-oil liquid emulsion), solutions, liquid dosage forms suitable for intradermal or subcutaneous administration to a patient.

In a further embodiment of the invention, the active ingredient of the invention may be delivered by a vehicle such as vesicles, biopolymers, liposomes, nanoparticles, microspheres, micelles, or virus incorporated. Biodegradable needles can also be used for the delivery of the YopM active ingredient via intradermal or subcutaneous administration.

The pharmaceutical composition can be used in the preparation of individual, single unit dosage forms. Pharmaceutical compositions and dosage forms of the invention can further comprise one or more carriers, excipients or diluents.

The composition, shape and type of dosage forms of the invention will typically vary depending on their use. For example, a dosage form used in the acute treatment of psoriasis disease may contain larger amounts of the active ingredients than a dosage form used in the chronic treatment of the same disease.

The pharmaceutical formulations can also be delayed release or controlled release formulations. YopM of the invention can be administered by delayed or controlled release means or by delivery devices that are well known to those of ordinary skill in the art.

\* \* \*

This disclosure may best be understood in conjunction with the accompanying figures, incorporated herein by references. Furthermore, a better understanding of the present invention and of its many advantages can be derived from the following examples, which are given by way of illustration and are not intended as limiting the disclosure.

4. FIGURES

FIG. 2a) is the SDS-PAGE analysis following isolation and purification of YopM. Proteins were separated on a 12.5%

SDS polyacrylamide gel and subsequently silver stained. lane M: "See Blue Plus2" protein ladder, RE: crude extract, W: wash I, lanes E2-5: elution fractions 2-5. FIG. 2b) shows the LPS content in YopM elution fractions by Limulus amebocyte lysate Toxin sensor assay.

FIG. 3c) refers to the results obtained on mice after a i.p. 100 µg of YopM in PBS every 48 h, FIG. 3e) shows the results obtained on mice treated with an YopM-containing cream (mice balmed with 200 mg cream containing approx. 30 µg of YopM); FIG. 3f) shows the results obtained on mice treated with YopM by subcutaneous injection (s.c. 25 µg in PBS every 48 h). FIG. 3a) is the negative control (untreated mice) and FIG. 4d) is the placebo control (200 mg cream without YopM).

FIG. 4a) refers to the negative control; FIG. 4b) to the IMQ-positive control; FIG. 4c) to the YopM intraperitoneally injected; FIG. 4d) to the placebo, FIG. 4e) to the YopM balmed, and FIG. 4f) to the YopM subcutaneously injected. Pictures were taken with confocal laser scanning microscope. Magnification 40×.

FIG. 5a) refers to negative control; FIG. 5b) to the IMQ-positive control; FIG. 5c) refers to the YopM intraperitoneally injected; FIG. 5d) refers to the YopM balmed. Pictures were taken with confocal laser scanning microscope. Magnification 40×.

(a) healthy skin; (b) untreated IMQ-skin; (c) placebo control; (d) YopM applied epicutaneously; (e) 12.5 µg YopM subcutaneously injected; (f) (e) 100 µg YopM subcutaneously injected. Pictures were taken with a light microscope. Magnification 40×.

5. EXAMPLES

To investigate whether YopM might be functional as an immune-modulator for the treatment of psoriasis, the murine imiquimod (IMQ)-induced psoriasis model has been utilized. In this model, daily topical application of imiquimod (IMQ), a TLR7/8 ligand and potent immune activator, on shaven mouse back skin induces and exacerbates a psoriasis-like condition ((Van der Fits L, et al. (2009) Imiquimod-induced psoriasis-like skin inflammation in mice is mediated via the IL-23/IL-17 axis. J. Immunol. 182: 5836-5845). Therefore, this model might serve for the analysis of pathogenic mechanisms in psoriasis-like dermatitis. Nestle and Nickoloff (Nestle, F. O., and B. J. Nickoloff. (2006) Animal models of psoriasis: a brief update. J. Eur. Acad. Dermatol. Venereol. 20(Suppl. 2): 24-27) defined several criteria for an ideal psoriasis model: 1) epidermal changes based on keratinocyte hyperproliferation and altered differentiation; 2) papillomatosis; 3) presence of inflammatory cells including T cells, DC, and neutrophils; 4) a functional role for T cells; 5) and altered vascularity. As the Imiquimod-induced psoriasis like skin model fulfils these criteria, it might serve for the analysis of pathogenic mechanisms in psoriasis-like dermatitis (Van der Fits L, et al. (2009) Imiquimod-induced psoriasis-like skin inflammation in mice is mediated via the IL-23/IL-17 axis. J. Immunol. 182: 5836-5845). For this, we applied YopM either epicutaneously (e.c.) as a component of a specific cream (e.c.) or by subcutaneous (s.c.) injection (every 48 h) over a period of two weeks to groups of mice suffering from Imiquimod-induced psoriasis. Furthermore, an additional group of psoriasis-mice was treated with YopM by intraperitoneally injection (i.p.).

5.1 Expression and Purification of Recombinant YopM in *E. Coli* BL21

Figure 1:
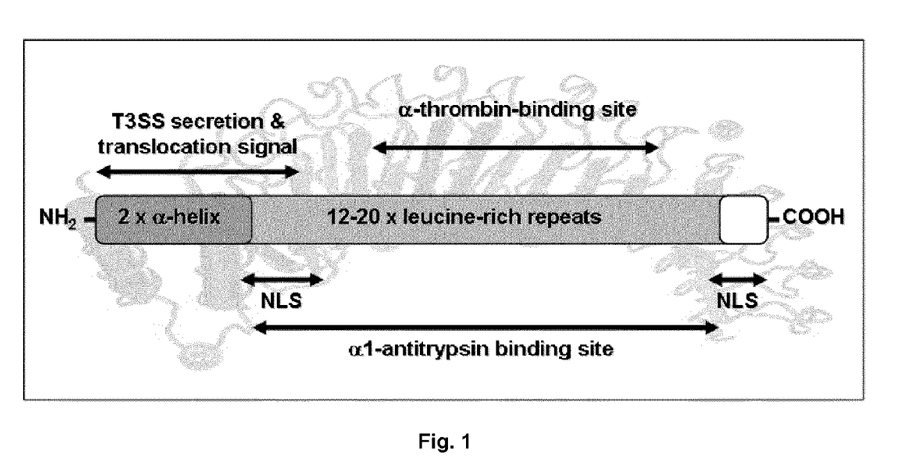
FIG. 1: discloses the domain organization and functional regions of YopM. Type-III secretion (S) and translocation (T) signal required by the T3SS [N-terminal residues aa 34-40 (S) & aa 40-100 (T), (Ghosh 2004)]. NLS, nuclear localization signal. NLS-I: three N-terminal LRRs and NLS-II: 32 C-terminal residues of YopM. Interaction with serum proteins α-thrombin and α1-antitrypsin seems to depend on conserved residues in LRR domains and not on specific domains of the LRR-containing region of the protein. The figure describes information gained from analyses of YopM from all three pathogenic Yersinia species.

For the expression of recombinant YopM (rYopM), the pET24b(+) expression vector which also provides the coding sequence for a C-terminal 6×His-tag has been chosen. Protein purification was performed by nickel-nitrilotriacetic acid (Ni-NTA) metal-affinity chromatography under native conditions. After purification, fractions of highest purity were pooled and dialyzed in PBS or H$_2$O bidest. The protein solution was applied to a dialysis tube (pore size: 6-10 kDa) and dialyzed overnight in 2 l PBS or H$_2$O bidest. at 4° C. with gentle stirring. After dialysis, the protein was concentrated using centrifugal filters at 500×g and 4° C. The expressed and purified recombinant proteins were quantified using the bicinchoninic acid (BCA) assay (Smith et al., 1985). Successful purification was confirmed by SDS-PAGE analysis. Proteins were separated on a 12.5% SDS polyacrylamide gel and subsequently silver stained (exemplified in FIG. 1a). Furthermore, the LPS content in elution fractions of recombinant YopM was determined by Limulus amebocyte lysate Toxin sensor assay (exemplified in FIG. 1b, approx. 0.33 EU/mg).

5.2 Effects of YopM on an Imiquimod (IMQ)-Induced Murine Psoriasis Model

Figure 2:
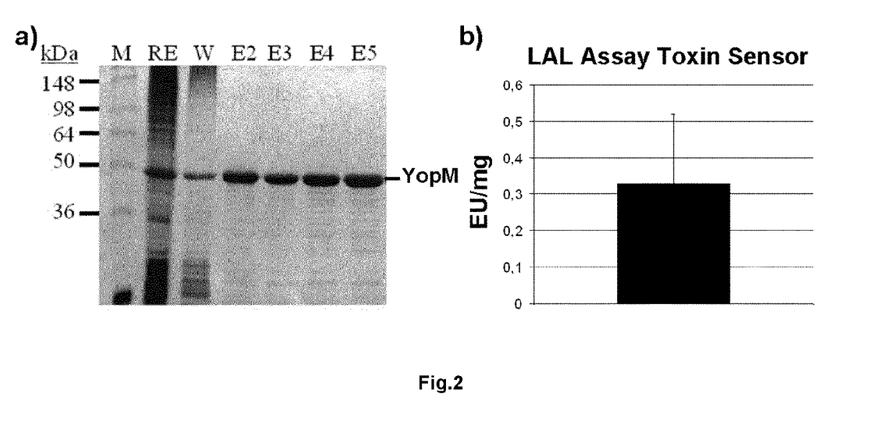
FIG. 2: refers to the purification of recombinant YopM.

The impact of rYopM applied topically (balmed and s.c.) and i.p. on inflammation linked to psoriasis-like conditions induced by imiquimod (FIG. 2) was investigated.

Daily epicutaneous (e.c.), topical application of imiquimod (IMQ) (5% Aldara Creme Sachets), a TLR7/8 ligand and potent immune activator, on mouse back skin (Balb/c)

induces and exacerbates psoriasis. After induction of psoriatic skin by IMQ, injections (i.p. and s.c.) of YopM (in PBS) into IMQ-treated Balb/c mice were performed every 48 h. Furthermore, YopM (in H₂O bidest.) was emulsified in a cream (150 µg YopM per 1 g cream).

Said cream contained cetearyl alcohol, paraffinum liquidum, glycerol, dimethicone, sodium cetearyl sulfate, phenoxyethanol, methylparaben, ethylparaben, propylparaben, and sodium hydroxide. Mice were balmed with 200 mg YopM-containing cream (approx. 30 µg of YopM) every 48 h.

Figure 3:
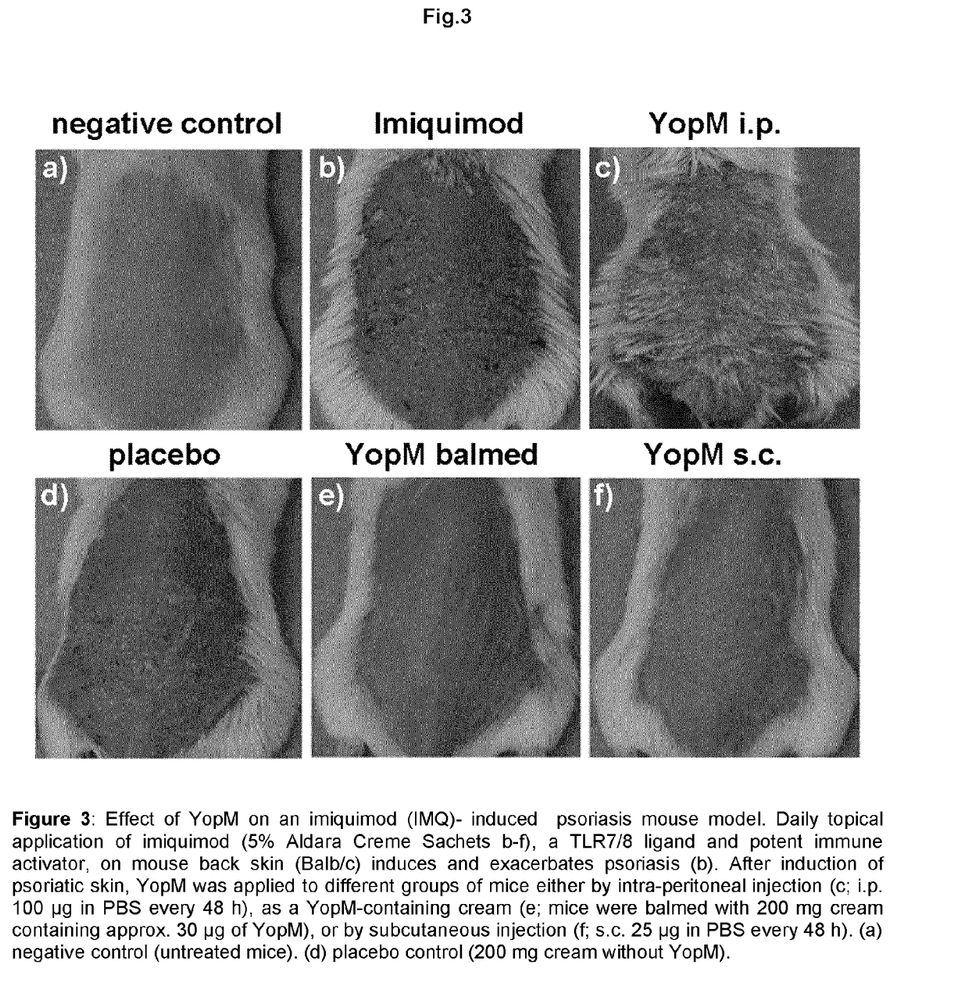
FIG. 3: shows the effect of YopM on an imiquimod (IMQ)-induced psoriasis mouse model. Daily topical application of imiquimod (5% Aldara Creme Sachets b-f), a TLR7/8 ligand and potent immune activator, on mouse back skin (Balb/c) induces and exacerbates psoriasis FIG. 3b).

In order to determine the beneficial effects of YopM on epidermal proliferation, abnormal differentiation, epidermal infiltrates consisting of CD4+ T cells, and papillomatosis induced by IMQ, we visually inspected the development of the psoriasis-like skin conditions. Pictures of the back skin of mice were taken after a period of two weeks (FIG. 3).

Figure 6:
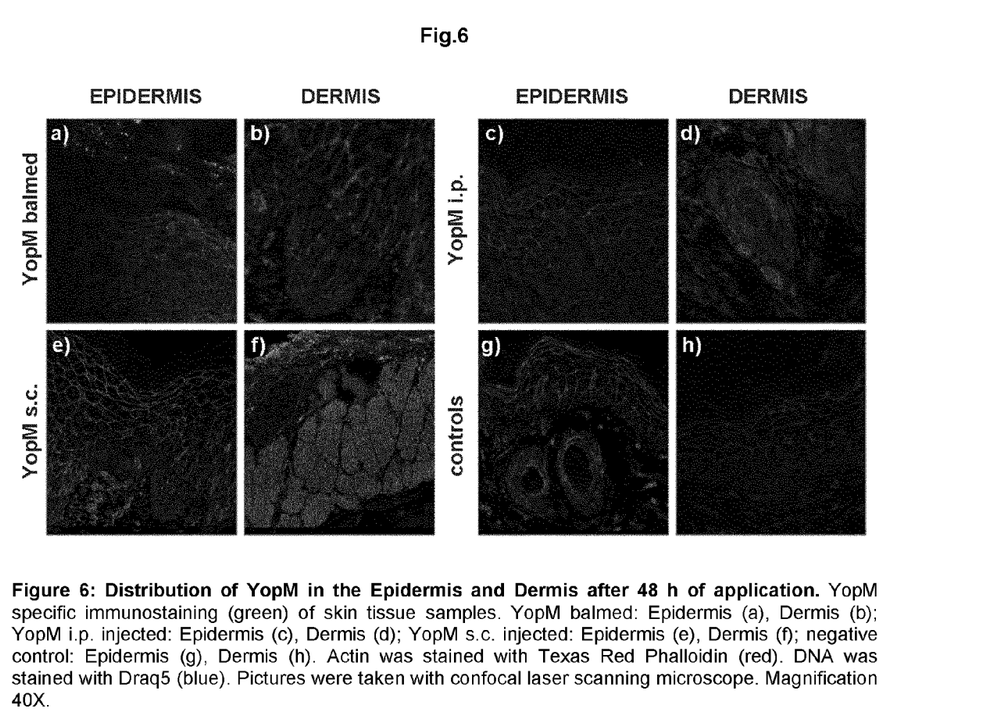
FIG. 6: Distribution of YopM in the Epidermis and Dermis after 48 h of application. YopM specific immunostaining (green) of skin tissue samples. YopM balmed: Epidermis (a), Dermis (b); YopM i.p. injected: Epidermis (c), Dermis (d); YopM s.c. injected: Epidermis (e), Dermis (f); negative control: Epidermis (g), Dermis (h). Actin was stained with Texas Red Phalloidin (red). DNA was stained with Draq5 (blue). Pictures were taken with confocal laser scanning microscope. Magnification 40×.
Figure 7:
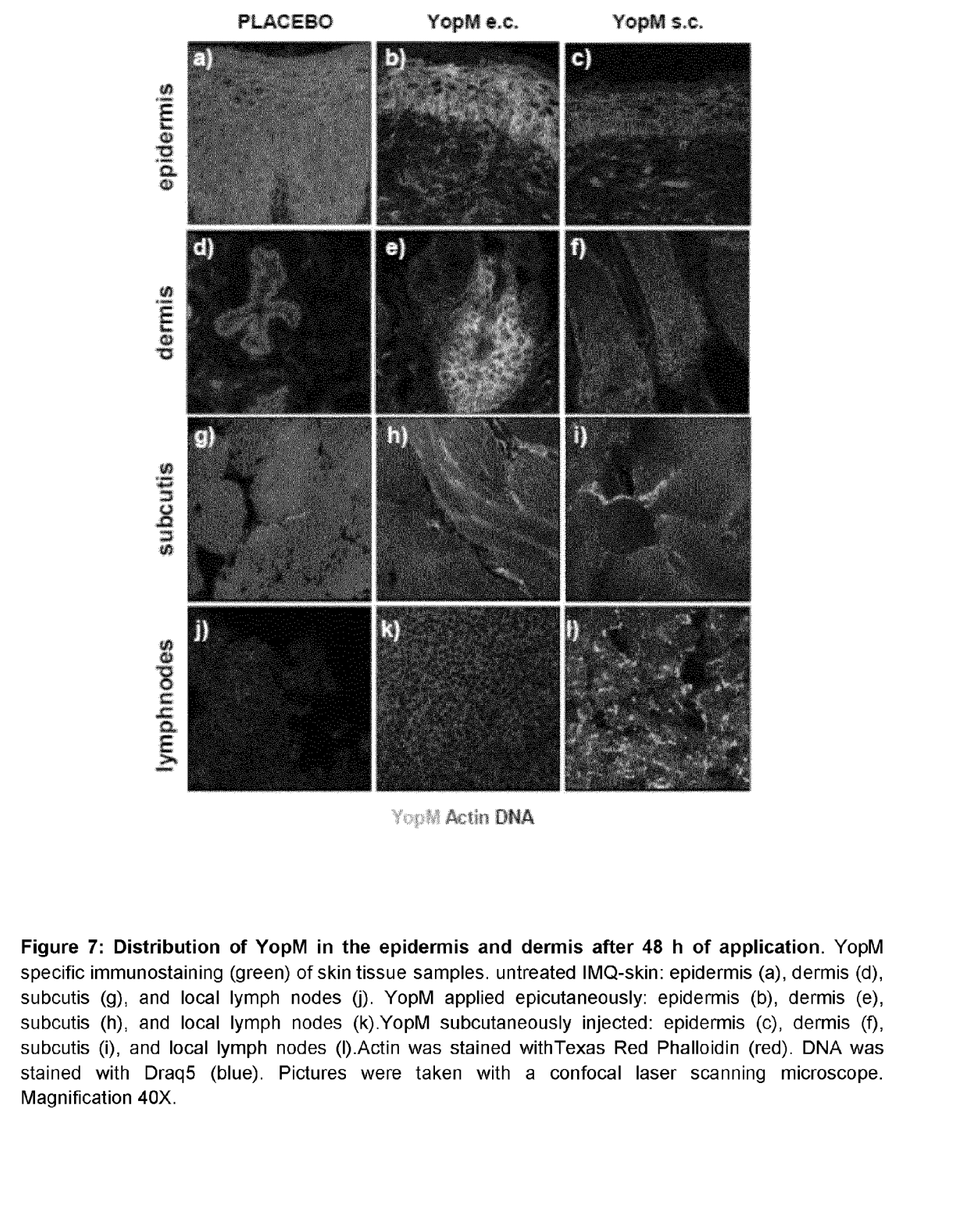
FIG. 7: Distribution of YopM in the epidermis and dermis after 48 h of application. YopM specific immunostaining (green) of skin tissue samples. untreated IMQ-skin: epidermis (a), dermis (d), subcutis (g), and local lymph nodes (j). YopM applied epicutaneously: epidermis (b), dermis (e), subcutis (h), and local lymph nodes (k).YopM subcutaneously injected: epidermis (c), dermis (f), subcutis (i), and local lymph nodes (l).Actin was stained with Texas Red Phalloidin (red). DNA was stained with Draq5 (blue). Pictures were taken with a confocal laser scanning microscope. Magnification 40×.
Figure 8:
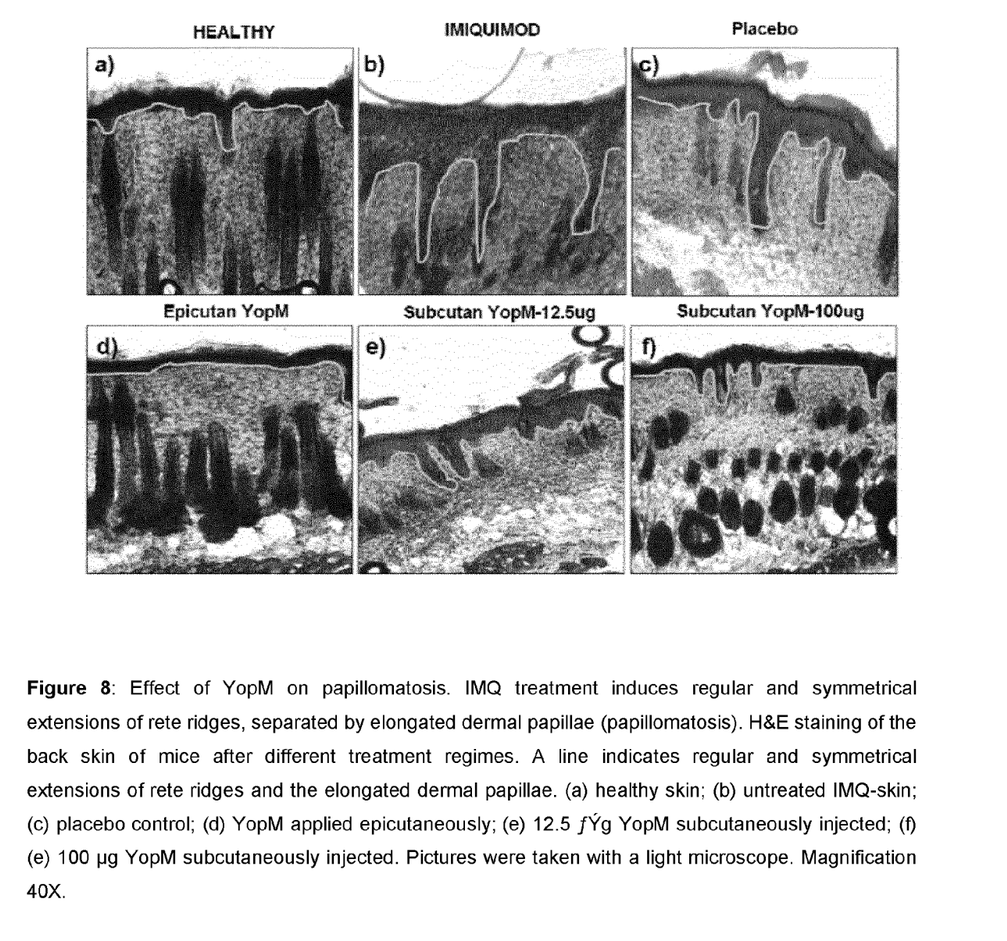
FIG. 8: Effect of YopM on papillomatosis. IMQ treatment induces regular and symmetrical extensions of rete ridges, separated by elongated dermal papillae (papillomatosis). H&E staining of the back skin of mice after different treatment regimes. A line indicates regular and symmetrical extensions of rete ridges and the elongated dermal papillae.

Further, immunohistochemistry staining on cryosections of biopsy taken from back skin of treated mice and employing antibodies against YopM (FIG. 6) has been performed. In particular, the distribution of YopM in the epidermis and dermis after 48 h of application has been determined. YopM balmed: Epidermis (a), Dermis (b); YopM i.p. injected: Epidermis (c), Dermis (d); YopM s.c. injected: Epidermis (e), Dermis (f); negative control: Epidermis (g), Dermis (h). Actin was stained with Texas Red Phalloidin (red). DNA was stained with Draq5 (blue).

Figure 4:
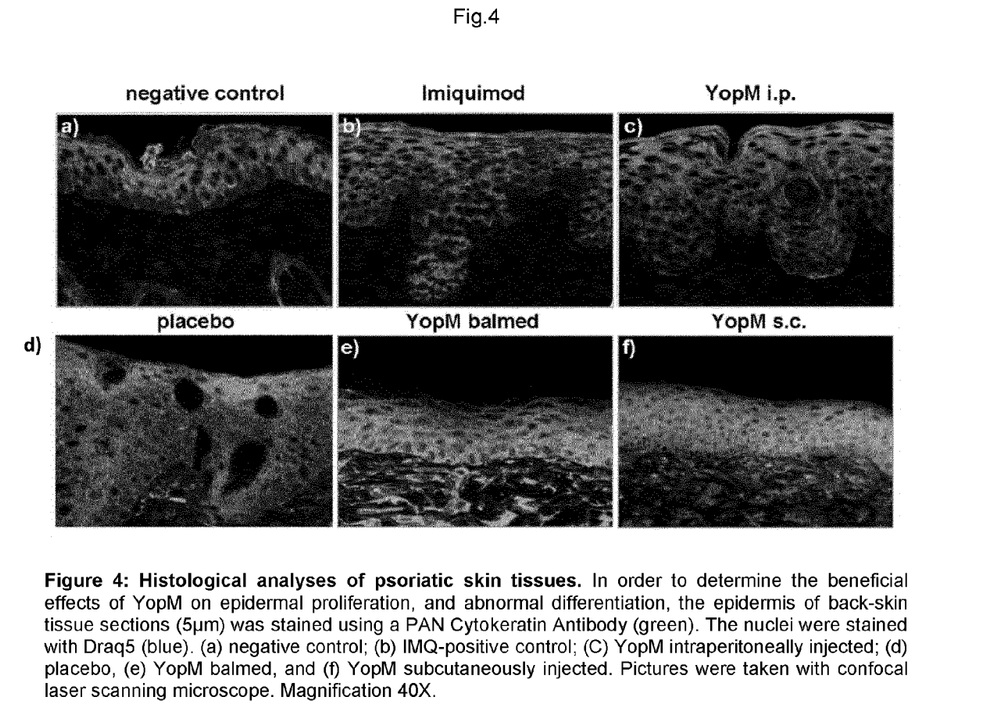
FIG. 4: refers to the histological analyses of psoriatic and non-psoriatic epidermis of back-skin tissue sections (5 µm) stained using a PAN Cytokeratin Antibody (green) to determine the beneficial effects of YopM on epidermal proliferation, and abnormal differentiation. The nuclei were stained with Draq5 (blue).

As further histological analyses of psoriatic and non psoriatic epidermis of back-skin tissue skin tissues was performed using a PAN Cytokeratin Antibody (green) in order to identify keratinocytes and to determine the beneficial effects of YopM on epidermal proliferation, and abnormal differentiation (FIG. 4). The epidermis of back-skin tissue sections (5 µm) was stained using a PAN Cytokeratin Antibody (green). The nuclei were stained with Draq5 (blue). FIG. 4a) is the negative control; FIG. 4b) is the IMQ-positive control; FIG. 4c) is the YopM intraperitoneally injected; FIG. 4d) refers to the placebo, FIG. 4e) is YopM balmed, and FIG. 4f) refers to the YopM subcutaneously injected.

Figure 5:
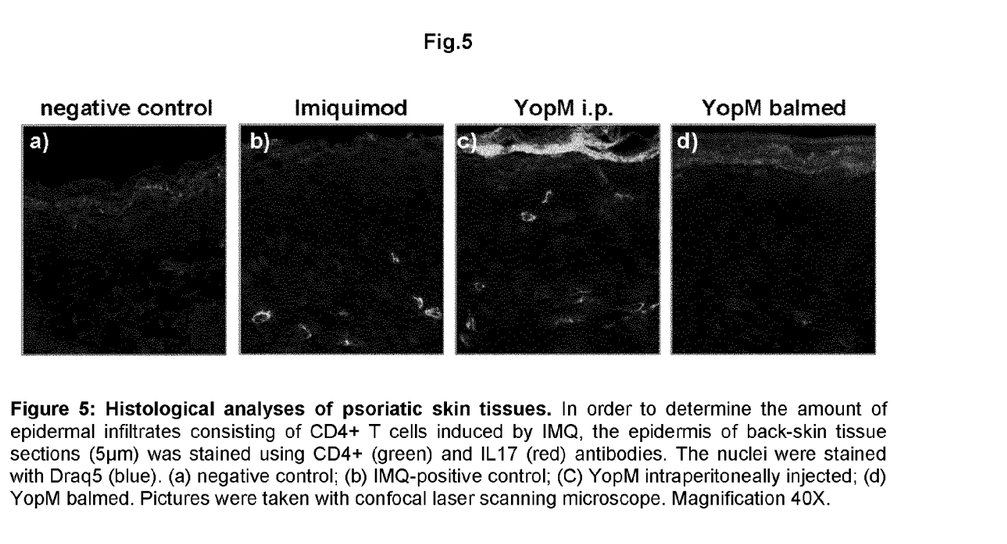
FIG. 5: shows the histological analyses of psoriatic and non psoriatic epidermis of back-skin tissue sections (5 µm) stained using CD4+ (green) and IL17 (red) antibodies to determine the amount of epidermal infiltrates consisting of CD4+ T cells induced by IMQ, the epidermis of back-skin tissue sections (5 µm) was stained using CD4+ (green) and IL17 (red) antibodies. The nuclei were stained with Draq5 (blue).

A further additional histological analysis of psoriatic and non psoriatic epidermis of back-skin tissue sections of the treated mice was performed in order to determine the amount of epidermal infiltrates consisting of CD4+ T cells induced by IMQ (FIG. 5). The epidermis of back-skin tissue sections (5 µm) was stained using CD4+ (green) and IL17 (red) antibodies. The nuclei were stained with Draq5 (blue). FIG. 5a) is the negative control; FIG. 5b) refers to IMQ-positive control; FIG. 5c) refers to the YopM intraperitoneally injected and FIG. 5d) to the YopM balmed.

The results confirm the "self-delivering" abilities of YopM across the cutaneous barrier when applied epicutaneously (e.c.) as a cream (FIG. 6a), b)), and already indicated a remarkable dampening of overt inflammatory reactions (FIG. 3e), 4e), 5d)). Repression of disease symptoms was also found in the group of mice subcutaneously injected with YopM (FIG. 3f), 4f), 6e) and 6f), whereas no significant phenotypic changes were observed in intraperitoneally injected mice (FIG. 3c), 4c), 5c), 6c) and 6d)). Interestingly, in contrast to s.c. treated mice, epicutaneously applied YopM did not enter systemic distribution, mainly remained in the epidermis, dermis, and subcutis, and couldn't be found in local lymph nodes. As s.c. injected YopM was also found in local lymph nodes, an epicutaneous treatment with YopM is clearly advantageous and favoured to avoid unwanted side effects.

These results clearly demonstrate a superior effect of the YopM-containing formulation or direct application of rYopM vs. control in cutaneous (e.c. and s.c.) vs. an i.p. application in reducing psoriasis-like conditions in a murine psoriasis model. Subsequent to cutaneous YopM application in the murine psoriasis model we observed nearly no detrimental epidermal changes based on keratinocyte hyperproliferation, lack of papillomatosis, and depletion of inflammatory T cells.

The invention claimed is:

1. A method for treatment of psoriasis in a human subject, comprising a step of administering a pharmaceutical composition comprising *Yersinia* outer protein M (YopM) to a human subject cutaneously, wherein administering treats the psoriasis wherein YopM does not enter the lymph node, and wherein the step of administering provides YopM in an amount in the range of 1 µg/cm² to 20 mg/cm² (YopM/cutaneous area).

2. The method according to claim 1 wherein the psoriasis is selected from the group consisting of plaque psoriasis, guttate psoriasis, inverse psoriasis, pustular psoriasis, erythrodermic psoriasis, and arthritis psoriasis.

3. The method according to claim 1 wherein the YopM is from a species selected from the group consisting of *Yersinia enterocolitica, Yersinia pseudotuberculosis* or *Yersinia pestis*.

4. The method according to claim 1, wherein the *Yersinia* outer protein M (YopM) is provided in a cream, lotion, gel or ointment.

5. The method according to claim 4, wherein the cream is a semi-solid emulsion.

6. The method according to claim 4, wherein the cream is an oil-in water or water-in oil cream.

7. The method according to claim 1, wherein the composition further comprises one or more of carriers, excipients, or diluents.

8. The method according to claim 1, wherein the composition further comprises one or more of cetearyl alcohol, paraffinum liquidum, glycerol, dimethicone, sodium cetearyl sulfate, phenoxyethanol, methylparaben, ethylparaben, propylparaben, and sodium hydroxide.

9. The method according to claim 1, wherein the amount is in the range of 1 µg/cm² to 20 µg/cm².

10. The method according to claim 9, wherein the amount is 2 µg/cm².

11. The method according to claim 1, wherein the step of administering is performed every 12 hours, or every 24 hours.

* * * * *